United States Patent
Jahns

(10) Patent No.: US 12,404,217 B2
(45) Date of Patent: Sep. 2, 2025

(54) PROCESS FOR TREATING A POROUS DENTAL ZIRCONIA BLOCK WITH COLORING SOLUTIONS

(71) Applicant: Solventum Intellectual Properties Company, Maplewood, MN (US)

(72) Inventor: Michael Jahns, Gilching (DE)

(73) Assignee: Solventum Intellectual Properties Company, Maplewood, MN (US)

( * ) Notice: Subject to any disclaimer, the term of this patent is extended or adjusted under 35 U.S.C. 154(b) by 167 days.

(21) Appl. No.: 17/755,445

(22) PCT Filed: Nov. 23, 2020

(86) PCT No.: PCT/IB2020/061033
§ 371 (c)(1),
(2) Date: Apr. 29, 2022

(87) PCT Pub. No.: WO2021/105848
PCT Pub. Date: Jun. 3, 2021

(65) Prior Publication Data
US 2022/0402830 A1    Dec. 22, 2022

(30) Foreign Application Priority Data
Nov. 26, 2019   (EP) ..................................... 19211435

(51) Int. Cl.
*C04B 41/45*   (2006.01)
*A61C 13/00*   (2006.01)
(Continued)

(52) U.S. Cl.
CPC ...... *C04B 41/4535* (2013.01); *A61C 13/0022* (2013.01); *C04B 35/48* (2013.01);
(Continued)

(58) Field of Classification Search
CPC .......... A61C 13/0022; A61C 2201/002; C04B 41/4535; C04B 35/48; C04B 35/0072; C04B 2235/3217; C04B 2235/3225
(Continued)

(56) References Cited

U.S. PATENT DOCUMENTS 6,709,694 B1 * 3/2004 Suttor .................... A61K 6/818
427/372.2
7,985,119 B2   7/2011 Basler et al.
(Continued)

FOREIGN PATENT DOCUMENTS

CN   104909745 B      3/2017
CN   108585845 A  *  9/2018
(Continued)

OTHER PUBLICATIONS

International Search Report for PCT International Application No. PCT/IB2020/061033, mailed on Jan. 12, 2021, 5 pages.

*Primary Examiner* — Brian K Talbot

(57) ABSTRACT

Process for treating a porous dental zirconia block with a coloring solution, the process comprising the steps of providing a porous dental zirconia block having two opposing surfaces, surface U and surface L, treating the upper surface U of the porous dental zirconia block with a coloring solution $A_1$, wherein the coloring solution is provided with a volume $VA_1$, turning the porous dental zirconia block around, treating the lower surface L with a coloring solution $A_2$ which is provided with a volume $VA_2$, wherein the coloring solutions $A_1$ and $A_2$ comprise a solvent and coloring ions, wherein the volume of at least one of the coloring solutions $A_1$ or $A_2$ is applied in portions, wherein the following condition is met: $Vo = \Sigma V_{Ax}$, with $x \geq 2$, with Vo being the overall amount of coloring solution used to infiltrate the porous dental zirconia block.

13 Claims, 1 Drawing Sheet

Figure 1:
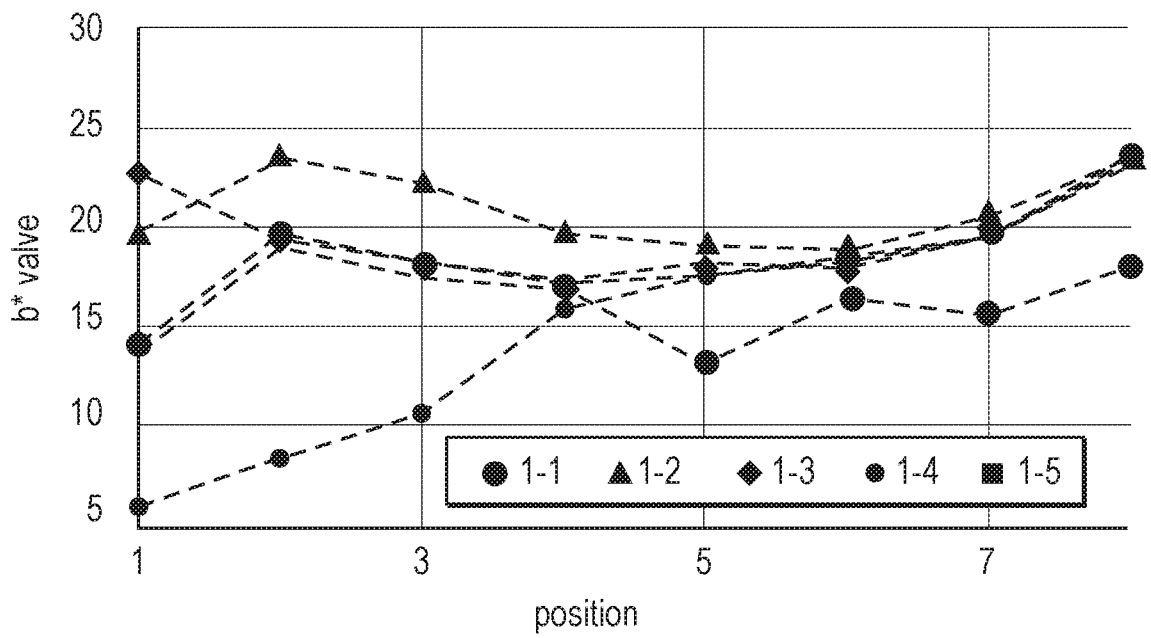

(51) Int. Cl.

| | |
|---|---|
| *C04B 35/48* | (2006.01) |
| *C04B 41/00* | (2006.01) |
| *C04B 41/50* | (2006.01) |
| *C04B 41/82* | (2006.01) |
| *C04B 41/85* | (2006.01) |

(52) U.S. Cl.
CPC ...... *C04B 41/0072* (2013.01); *C04B 41/5012* (2013.01); *C04B 41/82* (2013.01); *C04B 41/85* (2013.01); *A61C 2201/002* (2013.01); *C04B 2235/3217* (2013.01); *C04B 2235/3225* (2013.01); *C04B 2235/3244* (2013.01); *C04B 2235/77* (2013.01); *C04B 2235/9661* (2013.01)

(58) Field of Classification Search
USPC ........................................................ 427/2.26
See application file for complete search history.

(56) References Cited

U.S. PATENT DOCUMENTS

| | | | |
|---|---|---|---|
| 8,141,217 B2 | 3/2012 | Gubler et al. | |
| 8,845,954 B2 * | 9/2014 | Kariya | C04B 35/6264 264/655 |
| 9,554,881 B2 * | 1/2017 | Wang | C08K 3/16 |
| 9,757,310 B2 * | 9/2017 | Jahns | A61K 6/824 |
| 9,872,746 B2 * | 1/2018 | Hauptmann | A61C 5/77 |
| 9,949,808 B2 | 4/2018 | Wolz | |
| 10,065,895 B2 * | 9/2018 | Franke | C04B 41/85 |
| 10,245,127 B2 | 4/2019 | Kim et al. | |
| 11,460,251 B2 * | 10/2022 | Weisbeck | F27B 17/025 |
| 2010/0032086 A1 * | 2/2010 | Hwang | C04B 41/89 156/268 |
| 2015/0223917 A1 * | 8/2015 | Herrmann | C04B 41/009 428/210 |
| 2015/0289954 A1 * | 10/2015 | Chang | A61C 13/0004 433/29 |
| 2015/0297466 A1 * | 10/2015 | Jahns | A61K 8/0241 106/35 |
| 2017/0273765 A1 | 9/2017 | Jung | |
| 2017/0304031 A1 * | 10/2017 | Jung | A61C 13/082 |
| 2019/0126306 A1 * | 5/2019 | Bakhshaei | B05B 15/55 |
| 2019/0233340 A1 * | 8/2019 | Kim | C04B 41/5007 |
| 2022/0015879 A1 * | 1/2022 | Jung | A61C 13/0022 |

FOREIGN PATENT DOCUMENTS

| | | |
|---|---|---|
| DE | 20316004 U1 | 3/2004 |
| EP | 3178463 A1 | 6/2017 |
| JP | 2012162713 A | 8/2012 |
| WO | 2001013862 A1 | 3/2001 |
| WO | 2002045614 A1 | 6/2002 |
| WO | 2017144644 A1 | 8/2017 |
| WO | 2018225934 A1 | 12/2018 |

\* cited by examiner

PROCESS FOR TREATING A POROUS DENTAL ZIRCONIA BLOCK WITH COLORING SOLUTIONS

CROSS REFERENCE TO RELATED APPLICATIONS

This application is a national stage filing under 35 U.S.C. 371 of PCT/IB2020/061033, filed Nov. 23, 2020, which claims the benefit of European Application No. 19211435.3 filed Nov. 26, 2019, the disclosure of which is incorporated by reference in its/their entirety herein.

FIELD OF THE INVENTION

The invention relates a process for treating a porous dental zirconia block with coloring solutions, being applied in certain volumes.

The use of coloring solutions for treating the porous dental zirconia block allows for a more homogenous color gradient in the block after sintering. The inventive process is easy to conduct, as no control of environmental parameters is necessary, and produces no waste of the coloring solutions. Described is also a process of producing a dental restoration from such a porous dental zirconia block.

BACKGROUND

Recently, more and more dental zirconia materials suitable inter alia for a so-called chair-side process at a dental office enter the market, i.e. material which are used by the dentist in his office without involving a dental lab.

Main differentiators regarding the different zirconia materials seem to be sintering time, translucency and shade gradients, representing the dentists' need for time efficient processes and esthetic materials.

One way to increase the translucency of zirconia is to increase the amount of yttria-doping. A higher yttria-doping has typically an influence on the crystal structure of the zirconia material after sintering.

Usually, shaded or colored zirconia shows a translucency that is lower compared to the pure, unshaded material. One reason for this is, that the color introduced by coloring components causes absorption of certain wavelengths, thereby decreasing the amount of the overall transmitted light. This effect cannot be avoided, since it is inherent for the chosen color.

However, it was found that the chosen raw materials often also have an influence on the resulting translucency.

Currently, many of the pre-colored dental zirconia mill blanks with a color gradient are produced by using and mixing colored powders with non-colored zirconia powder.

These colored powders are not always compatible with the non-colored zirconia material (e.g. in view of different yttria content, different grain size, different primary particle size). This incompatibility is sometimes negligible, under the proviso that the sintering process is sufficiently long.

If, however, faster sintering processes are desired, this incompatibility may become more relevant.

For so-called chair-side zirconia materials, particular speed-sinterable grades are chosen. These typically allow for a good translucency after a short sintering time (<20 min).

However, when these non-colored powders are mixed with colored powders that are not speed-sinterable, the sintering time has to be increased to still obtain a good translucency.

Colored powders typically contain coloring components in the form of oxide particles. These particles usually need a longer sintering time in order to properly diffuse into the zirconia lattice.

One work-around would be to provide colored powders the specification of which is based on or adjusted to the speed-sinterable non-colored grades. This should maintain the speed-sinterability of the non-colored material.

However, in such a case a special set of colored powders is needed for every kind of non-colored zirconia grade. This would lead to a lot of part numbers, purchased in lower volume, and result in high raw material cost. It also would not change the diffusion time needed for the shading element oxides to enter the zirconia lattice.

Overall, various concepts are described in the literature:

CN 104 909 745 BB (Chengdu Besmile Biotech.) describes a preparation method to obtain uniform gradient-color zirconium oxide porcelain blocks. The preparation method comprises the steps: (1) weighing the raw materials of $CeO_2$, $Fe_2O_3$, $ZrO_2$, $Y_2O_3$, $Pr_6O_{11}$ and $Er_2O_3$; (2) adding a polymer binder, and granulating; (3) shaping the granulated material; (4) carrying out isostatic cool pressing; (5) pre-sintering the porcelain block blanks; (6) flatly placing the pre-sintered porcelain block blanks in a dyeing container and dyeing, wherein certain conditions are applied; and (7) sintering the dyed porcelain blocks to obtain the uniform gradient-color zirconium oxide porcelain blocks for dentistry.

CN 108 585 845 A (Bloomden Bioceramics) describes a method for preparing a zirconium oxide ceramic blank with gradual change of color and permeability. The method comprises the steps: (1) preparing a soluble yttrium solution, soaking one side of a pre-sintered zirconium oxide ceramic into a solution liquid level, exerting negative pressure to the other side of the zirconium oxide ceramic, and controlling a reduction velocity of the solution liquid level according to a preset pressure-time curve till the liquid level is reduced to a zero liquid level; (2) preparing a user-made16-color dyeing solution which meets 16 vita colors or a user-made 26-color dyeing solution which meets 26 vita colors, turning over the dried zirconium oxide ceramic for 180°, soaking one side of the zirconium oxide ceramic into a dyeing solution liquid level, exerting negative pressure to the other side of the zirconium oxide ceramic, and controlling a reduction velocity of the liquid level according to a preset pressure-time curve until the liquid level is reduced to a zero liquid level.

U.S. Pat. No. 9,949,808 B2 (Wolz) describes a process for producing a dental ceramic blank, having selectively adjustable degrees of expression of one or more different physical properties, wherein the ceramic body has a porosity to enable the control of a selective distribution of one or more chemical substances that are suitable for influencing the physical properties of the ceramic body, and in a first step the ceramic body is loaded with one or more solutions of the one or more chemical substances. In a second step the distribution of the one or more chemical substances within the porous ceramic body is controlled, wherein a progression and/or a spatial progression of the degree of expression of the one or more physical properties can be produced. The control is affected by adjusting one or more ambient parameters in an environment, in particular by adjusting the air humidity and/or the pressure and/or the temperature.

U.S. Pat. No. 10,245,127 B2 (Kim et al.) describes a method of manufacturing a multilayer zirconia block for artificial teeth, including a first material mixing step, a second material mixing step, a third material mixing step, a compression molding step, and a calcination step. This method is said to provide a multilayer zirconia block that contains yttrium oxide, the amount of which is adjusted in the manufacturing process, thus showing a color similar to that of natural teeth after impregnation with a coloring solution.

US 2017/0273765 A1 (Jung) describes a dental block for producing a dental prosthesis comprises a green body including zirconia and having a chemical composition including increasing amounts of a chroma component, such as manganese, through a thickness of the green body. The green body is substantially white with a substantially consistent optical characteristic of chroma across the thickness and is subsequently millable and sinterable to form the dental prosthesis with an optical characteristic of decreasing gray color through a thickness of the dental prosthesis.

WO 2018/225934 A1 (Park Tae Seok) describes a method for manufacturing a zirconia block for a dental prosthesis having a layered color gradient by water absorption rate. The permeation degree of a coloring solution is controlled by setting a different particle size of powder for each layer of the zirconia block on the basis of the property that the amount of water absorption per hour is differentiated according to the particle size of powder.

US 2019/0233340 A1 (Kim et al.) describes a method of coloring a ceramic body for use in dental applications. The method comprises the steps of obtaining a porous ceramic body comprising first and second end surfaces and a side surface, contacting various portions of the ceramic body with a casing material, infiltrating a diluting liquid to occupy a first porous region, adjusting the casing, infiltrating a liquid coloring composition to occupy a second porous region, wherein the casing material prevents the liquid coloring composition and diluting liquid from passing through the first end surface and side surface.

US 2015/0223917 A1 (Herrmann et al.) describes a kit of parts comprising a coloring solution, a porous zirconia article and optionally application equipment. Described is also a method for coloring and enhancing the translucency of a zirconia article wherein a coloring solution is applied to either only a part of the outer surface of the porous zirconia article or to the whole surface by dipping the zirconia article into the coloring solution.

However, none of the described process is completely satisfying. There is still a need for alternatives, which may help to either simplify or improve the existing processes.

SUMMARY OF INVENTION

As outlined above, the production of dental zirconia milling blocks by using layering techniques typically requires a lot of technical know-how.

Further, various kinds and grades of colored powders of zirconia material are typically needed.

As the colored powders often differ from each other with respect to particle size, yttria content, etc., the esthetics (in particular translucency) of the dental restoration obtained after milling and sintering may be affected. This holds in particular true, if a speed-sintering process is desired.

Providing differently colored zirconia powders having the same properties could be an alternative but will most likely be more expensive.

In view of the above, there is a need for a colored dental zirconia article optionally with a color gradient which allows the production of dental restorations with sufficiently high translucency (low contrast ratio) after sintering, even if a speed-sintering process is applied.

The process should be simple without the need for complicated apparatuses or adjustments.

Ideally, the desired dental zirconia restoration can be obtained within a short sintering time.

At least one of the above objects can be solved by the invention described in the present text.

In one embodiment the present invention features a process for treating a porous dental zirconia block with a coloring solution, the process comprising the steps of providing a porous dental zirconia block having two opposing surfaces, surface U and surface L, treating the upper surface U of the porous dental zirconia block with a coloring solution A1, wherein the coloring solution is provided with a volume VA1, turning the porous dental zirconia block around, treating the now upper surface L of the porous dental zirconia block with a coloring solution A2, wherein the coloring solution is provided with a volume VA2, wherein the coloring solutions $A_1$ and $A_2$ comprise a solvent and coloring ions, wherein coloring solution $A_1$ and coloring solution $A_2$ can be same or different, wherein the volume of at least one of the coloring solutions $A_1$ or $A_2$ is applied in portions, wherein the following condition is met: $\Sigma V_{Ax}$ with x≥2, in particular $V_0=V_{A1} V_{A2}$, with $V_0$ being the overall amount of coloring solutions used to infiltrate the porous dental zirconia block, as described in the present text and claims.

In another embodiment, the invention relates to a process of producing a dental restoration, the process comprising the steps of providing the porous dental zirconia block obtained or obtainable by the process described in the present text, machining a dental restoration from the porous dental zirconia block, sintering the dental restoration.

Unless defined differently, for this description the following terms shall have the given meaning:

The term "dental restoration" means an article which is to be used in the dental field to restore a defect tooth structure.

The dental restoration typically has a 3-dimensional inner and outer surface. The surface typically includes convex and concave structures. Compared to other articles such as pottery or paving stones, a dental restoration is small and filigree. The thickness of the dental restoration can vary from very thin, e.g. at the edges and rims (below 0.1 mm) to considerably thick, e.g. in the biting area (up to 8 or 16 mm). Sections bridging the crown portions in dental bridges might have a thickness up to 20 mm.

The outer surface typically has an overall convex shape, whereas the inner surface typically has an overall concave shape.

The dental restoration described in the present text comprises or essentially consists after sintering of a polycrystalline ceramic material comprising yttrium stabilized zirconia.

Examples of dental restorations include crowns (including monolithic crowns), bridges, inlays, onlays, veneers, facings, crown and bridged framework, abutments, orthodontic appliances (e.g. brackets, buccal tubes, cleats and buttons), and parts thereof.

The surface of a tooth is not regarded a dental article or dental restoration.

A dental restoration should not contain components which are detrimental to the patient's health and thus free of hazardous and toxic components being able to migrate out of the dental restoration.

By "dental mill blank or dental mill block" is meant a solid block (3-dim article) of material from which a dental restoration can and typically is to be machined in a subtractive process, e.g. aside from milling also by grinding, drilling etc.

A dental mill blank has a geometrically defined shape and comprises typically two opposing flat surfaces. A so-called "free form surface" is not regarded as "geometrically defined". In this respect, the shape of a dental restoration (e.g. crown or bridge) itself is not regarded a dental mill blank.

"Zirconia article" shall mean a 3-dimensional article wherein at least one of the x, y, z dimensions is at least 5 mm, the article being composed of at least 80 or at least 90 or at least 95 wt. % zirconia.

"Ceramic" means an inorganic non-metallic material that is produced by application of heat. Ceramics are usually hard, porous and brittle and, in contrast to glasses or glass ceramics, display an essentially purely crystalline structure.

"Crystalline" means a solid composed of atoms arranged in a pattern periodic in three dimensions (i.e., has long range crystal structure as determined by X-ray diffraction). Crystal structures include tetragonal, monoclinic, cubic zirconia and mixtures thereof.

"Glass" means an inorganic non-metallic amorphous material which is thermodynamically an under-cooled liquid. Glass refers to a hard, brittle, transparent solid. Typical examples include soda-lime glass and borosilicate glass. A glass is an inorganic product of fusion which has been cooled to a rigid condition without crystallizing. Most glasses contain silica as their main component and a certain amount of glass former and modifier.

"Glass-ceramic" means an inorganic non-metallic material where one or more crystalline phases are surrounded by a glassy phase so that the material comprises a glass material and a ceramic material in a combination or mixture. It is formed as a glass, and then crystallized by a nucleation and crystallization heat treatment. Glass ceramics may refer to a mixture of lithium-, silicon-, and aluminium-oxides.

The porous dental zirconia material described in the present text does not contain a glass or glass-ceramic.

A "powder" means a dry, bulk composed of a large number of fine particles that may flow freely when shaken or tilted.

A "particle" means a substance being a solid having a shape which can be geometrically determined. The shape can be regular or irregular. Particles can typically be analysed with respect to e.g. size and size distribution.

"Density" means the ratio of mass to volume of an object. The unit of density is typically $g/cm^3$. The density of an object can be calculated e.g. by determining its volume (e.g. by calculation or applying the Archimedes principle or method) and measuring its mass.

The volume of a sample can be determined based on the overall outer dimensions of the sample. The density of the sample can be calculated from the measured sample volume and the sample mass. The total volume of the material can be calculated from the mass of the sample and the density of the used material. The total volume of cells in the sample is assumed to be the remainder of the sample volume (100% minus the total volume of material).

A "porous material" refers to a material comprising a partial volume that is formed by voids, pores, or cells in the technical field of ceramics.

The term "calcining" refers to a process of heating a solid material to drive off at least 90 percent by weight of volatile chemically bound components (e.g. organic components) (vs., for example, drying, in which physically bound water is driven off by heating). Calcining is done at a temperature below a temperature needed to conduct a pre-sintering step.

The terms "sintering" or "firing" are used interchangeably. A porous ceramic article shrinks during a sintering step, that is, if an adequate temperature is applied. The sintering temperature to be applied depends on the ceramic material chosen. For $ZrO_2$ based ceramics a typical sintering temperature range is 1,100° C. to 1,600° C. If the sintering is done with high heating-rates, higher temperatures may be required. Sintering typically includes the densification of a porous material to a less porous material (or a material having less cells) having a higher density, in some cases sintering may also include changes of the material phase composition (for example, a partial conversion of an amorphous phase toward a crystalline phase).

A dental zirconia article is classified as "pre-sintered", if the dental zirconia article has been treated with heat (temperature range from 900 to 1,100° C.) typically for 1 to 3 h to such an extent that the biaxial flexural strength of the dental ceramic measured according to the "punch on three ball test" ISO 6872:2015 is within a range of 8 to 80 MPa or 15 to 55 MPa.

A pre-sintered dental ceramic usually has a porous structure and its density (usually about 3.0 $g/cm^3$ for an yttrium stabilized zirconia ceramic) is less compared to a completely sintered dental ceramic framework (usually about 6.1 $g/cm^3$ for an yttrium stabilized zirconia ceramic).

"Coloring ions" shall mean ions which have an absorption in the spectral range visible to the human eye (e.g. 380 to 780 nm), which may result in a colored solution (visible to the human eye), if the coloring ions are dissolved in water (e.g. about 0.6 mol/l) and especially cause a coloring effect in the zirconia article which has been treated with a coloring solution and sintered afterwards. Coloring ions may also be present (typically as component of a salt or oxide) in the powder before the powder, which is used for producing the zirconia article, is compacted.

A "fluorescing agent" shall mean an agent capable to impart fluorescence, measurable as light emission in the region of visible light (380 to 780 nm).

By "machining" is meant milling, grinding, cutting, carving, or shaping a material by machine. Milling is usually faster and more cost effective than grinding. A "machinable article" is an article having a 3-dimensional shape and having sufficient strength to be machined.

"Ambient conditions" mean the conditions which the composition described in the present text is usually subjected to during storage and handling. Ambient conditions may, for example, be a pressure of 900 to 1100 mbar, a temperature of 10 to 40° C. and a relative humidity of 10 to 100%. In the laboratory, ambient conditions are typically adjusted to 20 to 25° C., 1000 to 1025 mbar and 40 to 60% relative humidity (with respect to maritime level).

A composition is "essentially or substantially free of" a certain component, if the composition does not contain said component as an essential feature. Thus, said component is not wilfully added to the composition either as such or in combination with other components or ingredient of other components. A composition being essentially free of a certain component usually does not contain that component at all. However, sometimes the presence of a small amount of the said component is not avoidable e.g. due to impurities contained in the raw materials used.

As used herein, "a", "an", "the", "at least one" and "one or more" are used interchangeably. Also herein, the recitations of numerical ranges by endpoints include all numbers subsumed within that range (e.g., 1 to 5 includes 1, 1.5, 2, 2.75, 3, 3.80, 4, 5, etc.).

"And/or" means one or both. E.g., the expression component A and/or component B refers to a component A alone, component B alone, or to both component A and component B.

Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and so forth used in the specification and claims are to be understood as being modified in all instances by the term "about".

The terms "comprise" or "contain" and variations thereof do not have a limiting meaning where these terms appear in the description and claims. The term "comprise" shall include also the terms "consist essentially of" and "consist of". "Consisting essentially of" means that specific further components can be present, namely those which do not materially affect the essential characteristic of the article or composition. "Consisting of" means that no further components should be present.

DETAILED DESCRIPTION

It has been found that the processes described in the present text provide a couple of advantages.

By applying the process described in the present text, a sufficiently high translucent dental zirconia article can be produced.

The desired color and contrast ratio of the sintered dental zirconia article can be obtained faster compared to a sintered dental zirconia article produced by using differently colored zirconia powders.

By applying the process described in the present text, a higher translucency can be obtained without the need to increase the yttria content of the zirconia material, which may negatively affect the flexural strength of the sintered material.

In addition, the porous dental zirconia article obtained by the process described in the present text is highly suitable for being sintered by applying a speed-sintering process.

With the process described in the present text, a zirconia material of higher translucency in colored state can be obtained, which can also be sintered almost at the same speed as the non-colored zirconia material.

The process also allows the production of a colored dental zirconia article which is highly translucent and shows an adequate color gradient.

Thus, the use of coloring solutions as described in the present text has almost no negative impact on the properties of the basic non-colored zirconia material, since no different yttria content, grain size or primary particle size is introduced.

The coloring components can also be better distributed in the zirconia material compared to the distribution of color oxide particles in powders.

Compared to the processes described in the art, the process described in the present text is less complicated.

All that is basically needed are non-colored porous blocks of zirconia material and a set of coloring solutions with coloring components or ions (e.g. a set with solutions of salts of erbium (Er), terbium (Tb), chromium (Cr) and bismuth (Bi), or a set with solutions of salts of erbium (Er), iron (Fe) and manganese (Mn)), or a set with solutions of salts of erbium (Er), iron (Fe) and chromium (Cr)).

Another advantage of this technique is that by completely infiltrating the porous dental zirconia block the formation of air inclusions can be avoided. Air inclusions are typically not desired as they may lead to an inhomogeneous infiltration.

In contrast to process described e.g. in CN 108 585 845 A the process described in the present text does not require a regulation of environmental parameters (e.g. application of pressure or vacuum). There is also no need to seal or isolate certain sides of the porous blocks as proposed in or US 2019/0233340 A1 (Kim et al.) and no need to place the porous block in a bath of coloring solution that probably would have to be discarded after use.

Thus, the process described in the present text is also advantageous from an economic aspect, as it allows the production of porous dental zirconia blocks by using only the amount and volume of coloring liquids which is actually needed, without wasting raw materials.

The process of treating the porous zirconia block comprises the step of providing a porous dental zirconia block.

The porous dental zirconia block has two opposing surfaces, a surface U (which might be regarded as "upper surface") and a surface L (which might be regarded as "lower surface").

The porous dental zirconia block has a pore volume $V_B$.

The process of treating the porous zirconia block further comprises the step of providing a first coloring solution with a particular volume.

According to one embodiment, at least two coloring solutions, coloring solutions $A_1$ and coloring solution $A_2$, are provided, each with a certain volume.

The process of treating the porous zirconia block further comprises the step of treating the upper surface U of the porous dental zirconia block with the first coloring solution $A_1$. This can be achieved by simply dripping the solution onto surface U.

According to one embodiment, the coloring solutions are applied in portions. That is, e.g. the volume $V_{A1}$ of coloring solution $A_1$ is split and applied in consecutive steps. This may help to reduce the risk that the coloring solution is not absorbed by the upper surface completely but runs over the edge of the block and contaminates the side surfaces of the block. The height of free liquid on the upper surface can typically be in the range of up to 0.5 mm.

The coloring solution is typically dipped onto the upper side of the porous zirconia block, ideally onto the center of the surface, until the entire surface is covered. The solution typically spreads readily to the edges of the surface. After a short time, as infiltration has progressed, a further portion of the coloring solution can be applied.

The process of treating the porous zirconia block further comprises the step of turning the porous dental zirconia block around. By doing that the previous upper surface (U) becomes the lower surface and the previous lower surface (L) becomes the upper surface.

It can be beneficial to turn the porous dental zirconia block to the opposite side in the middle of the process, as this reduces the migration distance through the block.

The first treating step is typically done until about 10% or about 30% or about 50% or about 70% or about 90% of the pore volume of the block is soaked with coloring liquid.

The process of treating the porous zirconia block further comprises the step of treating surface L of the porous dental zirconia block with a further coloring solution. The further coloring solution may be same or different from the first coloring solution.

This raises the opportunity to use two different coloring solutions to provide e.g. an enamel and a body shading region in the block and to increase the overall esthetics of the dental restoration after sintering. If the coloring solution is changed without turning the block around (e.g. by using an optional third coloring solution $A_3$), the application of the new solution can be started when either the previous solution has been soaked completely into the block or when it is still free on the block surface. The first alternative will produce a sharper gradient while the second will produce a smoother gradient as the two solutions will already mix readily on the block surface.

If only one surface (e.g. surface U) of the porous dental zirconia block with a single coloring solution or with two or even more different coloring solutions is treated, a monochrome shade as well as a shade gradient can also be obtained. However, because of the long diffusion path, the time to infiltrate the entire block is unduly long and therefore not recommended for most manufacturing processes. Especially the last 10% of open pores typically take the longest time to be infiltrated, if the block is not turned around.

The coloring solutions are provided in certain volumes (e.g. coloring solution $A_1$ is provided with volume $V_{A1}$, coloring solution $A_2$ is provided with volume $V_{A2}$).

The coloring solutions are provided in volumes to meet the following condition:

$$V_0 = \Sigma V_{Ax} \text{ with } x \geq 2, \text{ in particular } V_0 = V_{A1} + V_{A2},$$

with $V_0$ being the overall amount of coloring solutions used to infiltrate the porous dental zirconia block.

$$\Sigma V_{Ax} \text{ with } x \geq 2 \text{ means } V_{A1} + V_{A2} + \ldots$$

This is in contrast to the processes described in the art so far, where a large and not defined volume of coloring solution is provided into which the porous zirconia material is typically placed.

In general, if more than two coloring solutions are used (e.g. $A_x$ with $x=1, 2, 3, \ldots$), the coloring solutions are used in respective volumes to meet the following conditions:

$$V_0 > V_{Ax} \text{ and}$$

$$V_0 = V_{A1} + V_{A2} + V_{A3} + \ldots$$

According to another embodiment, the process of treating the porous zirconia block may further comprise the step of applying a further coloring solution (e.g. coloring solution $A_3$), which is different from the first and second coloring solution (e.g. coloring solution $A_1$ and coloring solution $A_2$).

If used, coloring solution $A_3$ is applied to surface U of the porous dental zirconia block before the block is turned around.

Alternatively, coloring solution $A_3$ is applied to surface L of the porous dental zirconia block after the block has been turned around and before coloring solution $A_2$ is applied.

Alternatively, coloring solution $A_3$ is applied to surface L of the porous dental zirconia block after the block has been turned around and after coloring solution $A_2$ has been applied.

Applying a coloring solution $A_3$ in addition to a coloring solution $A_1$ and $A_2$ may help to further adjust the concentration of the coloring components in the porous dental zirconia block, in particular to obtain or to adjust a color gradient.

The process of treating the porous zirconia block may further comprise the step of immobilizing the coloring ions inside the porous dental zirconia block.

An immobilization step of the treated zirconia material is not absolutely necessary but can be preferred to reduce the time needed for sintering later and to avoid undesired color effects. The main purpose is to remove the solvent and the no longer needed anions from the porous dental zirconia block, thereby immobilizing the coloring ions.

Immobilization can be achieved by simply storing the article at ambient conditions for a couple of hours and removing the solvent by evaporation (e.g. 1 to 24 hours, depending on the size of the block and evaporating conditions used).

Alternatively, and sometimes preferred, the immobilization step is conducted by applying a heat treatment.

If a heat treatment is applied, the heat treatment is typically done at a temperature of at least 500° C. or at least 700° C. or at least 800° C. or at least 900° C.

The heat treatment is done for a time sufficient to dry the dental zirconia block and to remove any anions that were present in the coloring solution.

To enable an easier machining of the porous dental zirconia block afterwards, the heat treatment should not exceed the optimum pre-sintering temperature of the porous dental zirconia block.

Thus, the heat treatment is typically done below a temperature of 1,100° C. or below 1,000° C.

If a color gradient was introduced, it will be influenced by the amount of time until the ions are immobilized. More time will lead to a smoother gradient, since the ions can diffuse inside the block for a longer time. If the time is too long, however, the gradient might even almost disappear again, because the ion concentration gradient inside the block is equalized.

Coloring solution $A_1$ is typically provided in a volume $V_{A1}$. Coloring solution $A_2$ is typically provided in a volume $V_{A2}$. When following the treatment steps, the following conditions are met:

volume $V_0$ of the entirely used coloring solution for the block > volume $V_{A1}$ of coloring solution $A_1$, volume $V_0$ of the entirely used coloring solution for the block > volume $V_{A2}$ of coloring solution $A_2$, and volume $V_0$ of the entirely used coloring solution for the block = volume $V_{A1}$ of coloring solution $A_1$ + volume $V_{A2}$ of coloring solution $A_2$.

The porous dental zirconia block to be treated with the coloring solution(s) has pores which allows the absorption of a certain volume of coloring solution. That is, the pores need to be accessible for the coloring solution. These pores are typically regarded as "open-celled pores".

The porous dental zirconia block with two opposing surfaces has typically a geometrically defined shape.

Various shapes can be used, including the shape of a cube, cuboid, disc or cylinder. The surface that is treated with the coloring solution should be oriented horizontally, to ensure that the coloring solution does not run over the edge of the block and contaminates the side surfaces of the block.

If the porous dental zirconia mill blank has the shape of a block, the dental mill blank has typically the following dimensions:

x-dimension: 12 to 45 mm, or 14 to 40 mm,
y-dimension: 12 to 70 mm, or 14 to 60 mm,
z-dimension: 10 to 40 mm, or 12 to 25 mm.

If the porous dental zirconia mill blank has the shape of a disc, the dental zirconia mill blank has typically the following dimensions:

x, y-dimension: 90 to 110 mm, or 95 to 105 mm,
z-dimension: 5 to 35 mm, or 10 to 30 mm.

The pore volume of the porous dental zirconia blank is typically within a range of 0.12 to 0.18 ml/g or 0.13 to 0.17 ml/g.

Thus, the overall pore volume of a porous zirconia blank is typically in a range of 1 to 300 ml, 1.4 to 120 ml (for blocks) or 25 to 300 ml (for discs).

The porous dental zirconia block before the treatment process may be characterized by the following features alone or in combination:

a) BET surface: 5 to 20 m$^2$/g or 6 to 15 m$^2$/g;
b) density: 2.5 to 4 g/cm$^3$ or 2.85 to 3.35 g/cm$^3$;
c) average connected pore diameter: 20 to 150 nm.

The following combination of features is sometimes preferred: a) and b); a) and c); a), b) and c).

Using a material with an average connected pore diameter from 20 to 150 nm can be beneficial, because it is comparably easy to produce (e.g. by compacting a powder and conducting a pre-sintering step).

Alternatively, or in addition, the material of the porous dental zirconia article can be characterized by the following parameters alone or in combination:

a) flexural strength: 15 to 55 MPa determined according to ISO 6872:2015 adapted to measurement in porous state (measurement set up: 3.6 mm punch diameter, 0.1 mm/min load speed, 17 mm sample diameter, 2 mm sample thickness, support ball diameter 6 mm);
b) Vickers hardness: 15 to 150 (HV 0.5).

If desired and applicable, the respective features can be determined as described in the example section.

The material of the porous dental zirconia block comprises ceramic components and stabilizing components.

The ceramic components are typically selected from oxides of Zr, Hf, Al and mixtures thereof.

Thus, in addition to zirconia, the material of the porous zirconia dental block typically comprises oxides of Hf and optionally of Al; if present, Al$_2$O$_3$ typically in only small amounts.

Stabilizing component(s) are typically selected from oxides of Y, Mg, Ca, Ce and mixtures thereof (e.g. Y$_2$O$_3$, MgO, CaO, CeO$_2$), wherein oxides of Y are often preferred.

According to one embodiment, the material of the porous dental zirconia block comprises, essentially consists of or consists of the following components in the given amounts:

ZrO$_2$ content: 82 to 99 mol % or 87 to 96.8 mol %,
HfO$_2$ content: 0 to 2 mol % or 0.1 to 1.8 mol %,
Y$_2$O$_3$ content: 2 to 6 mol % or 3 to 6 mol %,
Al$_2$O$_3$ content: 0 to 1 mol % or 0.005 to 0.5 mol % or 0.01 to 0.2 mol %.

According to a further embodiment, the material of the porous dental zirconia block comprises, essentially consists of or consists of the following components in the given amounts:

ZrO$_2$ content: 91.8 to 97 mol %,
HfO$_2$ content: 0 to 2 mol %,
Y$_2$O$_3$ content: 3 to 6 mol %,
Al$_2$O$_3$ content: 0 to 0.2 mol %.

A higher Y$_2$O$_3$ content typically leads to an increase of the cubic crystal phase in the zirconia ceramic material after sintering the material to final density. A higher content of the cubic crystal phase may contribute to a higher translucency.

The material of the porous dental zirconia article described in the present text may contain about 3, 4 or 5 mol % yttria. These materials are sometime referred to as 3Y-TZP, 4Y-TZP or 5-YTZP materials.

It has been found that these materials are particularly useful for producing an aesthetic zirconia restoration in a firing process as described in the present text.

In another embodiment, the material of the porous dental zirconia article comprises:

ZrO$_2$+HfO$_2$: 88.85 to 95 wt. %;
Y$_2$O$_3$: 5 to 11 wt. %;
Al$_2$O$_3$: 0 to 0.15 wt. %;
wt. % with respect to the weight of the porous dental zirconia block.

There is no need for alumina to be present, however, the presence of a small amount of alumina may be beneficial as it may contribute to a better hydrothermal stability of the zirconia article after sintering.

However, too high an amount of alumina may have a negative impact on the translucency of the zirconia article after sintering.

Thus, alumina may be present in an amount of 0 to 0.15 wt. %, or 0 to 0.12 wt. % or 0 to 0.10 wt. %.

The material of the porous dental zirconia block does typically not comprise the following components alone or in combination before the firing process:

glass or glass ceramic;
oxides of Si, K, Na; in an amount above 1 wt. % with respect to the weight of the material of the
porous zirconia dental article.

The presence of these elements may negatively affect the overall performance of the porous dental zirconia article during machining or sintering of the machined articles.

The porous dental zirconia block to be colored can be produced by compacting zirconia powder, calcining the compact and optionally pre-sintering the compact.

Suitable metal oxide powders are commercially available from various sources including Tosoh Company (Japan).

To facilitate the compacting or pressing step, pressing aids can be added, if desired.

Suitable pressing aids include binders, lubricating additives and mixtures thereof.

The applied pressure is typically in the range of 150 to 300 MPa. Alternatively, the applied pressure is set so that the pressed ceramic body reaches a certain density, e.g. in the case of zirconia ceramic a density of 2.8 g/cm$^3$ to 3.5 g/cm$^3$.

If desired, a calcining step can be done.

The pore size and pore volume of the porous zirconia dental block can be adjusted by using an appropriate pressure during the pressing step and an appropriate temperature during the calcining/pre-sintering step.

E.g. a temperature in the range of 600° C. to 1,100° C. was found to be useful.

By using a lower temperature in this range, the pores of the porous dental zirconia block are typically larger compared to the pores obtained by applying a higher temperature in this range.

A larger pore size can be beneficial to facilitate the absorption of the coloring solutions during the treatment steps, e.g. by reducing the processing time.

A higher temperature can be beneficial to obtain a harder and thus more robust porous zirconia dental block. However, the time needed to completely infiltrate the block might be longer.

The heat treatment is typically applied for a duration of 10 to 70 hours or 15 to 60 hours.

The article obtained after heat treatment can be machined or sliced into any desired shape.

The process described in the present text comprises the step of treating opposing surfaces of the porous dental zirconia dental block with one or more coloring solutions.

The coloring solutions comprise coloring ions and a solvent for dissolving the coloring ions.

In certain embodiments the coloring solution fulfils at least one or more, sometimes all of the following parameters:
pH value: 0 to 9 or 1 to 8 or 2 to 7, if the coloring solution contains water;
viscosity: 1 to 20 mPa*s or 2 to 15 mPa*s or 3 to 10 mPa*s (measured at 23° C.);
being transparent;
being colored.

If desired, these parameters can be determined as outlined in the Example section.

If the solution is a water containing (aqueous) solution, it typically has a pH value in the range of 0 to 9, that is from strong acidic to slightly basic.

If the pH value of the solution is outside this range, it might be difficult to achieve a storage stable solution. In particular, the cations of the non-coloring agent might start to precipitate from the solution.

If the solution does not contain a complexing agent, a pH value in the acidic range is typically preferred.

If the solution, however, contains a complexing agent, the pH value may be in a range from slightly acidic to slightly basic (e.g. pH 5 to 9 or 6 to 9).

The coloring solution typically has an adequate viscosity so that a sufficient amount of solution can not only be applied to the surface of the zirconia article but also is able to migrate into the pores of the porous zirconia article.

Adjusting the viscosity to a value as indicated above can be beneficial in that the solution can be more accurately applied to the surfaces of the porous dental zirconia block.

If the viscosity of the solution is too high, the solution might not be able to sufficiently enter the pores of the zirconia material. On the other hand, if the viscosity of the solution is too low, the ions might migrate inside the pores too rapidly. Rapidly moving ions might lead to drying artefacts at the edges of the block.

In a further embodiment the solution is transparent.

In a further embodiment, the coloring solution shows light absorption in the range from 380 to 780 nm.

That means, the solution appears colored to the human eye (in contrast to e.g. water).

The coloring solutions contain a solvent for dissolving the coloring ions.

The nature of the solvent is not particularly limited unless the desired effect is not achieved. The solvent used is of a nature and present in an amount suitable for dissolving the components being present in the coloring solution, in particular the coloring ions.

The solvent is typically miscible with water.

The solvent is typically selected from water, alcohols (e.g. methanol, ethanol, propanol), polyalcohols (e.g. ethylene glycol, glycerol), ketons (e.g. propan-one, butan-one) and mixtures thereof, wherein water is often preferred.

The coloring solution also comprises one or more coloring ions.

The coloring ions are typically metal ions selected from the group of transition metals or rare earth elements of the periodic table of elements. The coloring ions are typically added during the process of producing the coloring solution in salt form comprising cations and anions.

Useful coloring ions may comprise or essentially consist of consist of only one of the following combinations: ions of Er, Pr, Cr, Fe, Mn or Tb or a combination thereof.

The following combinations are sometimes preferred: Er and Pr; Er and Cr; Er and Tb; Er and Fe; Pr and Cr; Fe and Mn; Tb and Cr; Tb and Mn; Er, Pr and Cr; Er, Tb and Cr; Er, Fe and Mn; Er, Fe and Cr; Er, Tb and Mn; Er, Pr, Tb and Cr; Er, Pr, Tb and Mn.

Praseodymium and terbium possess narrower absorption bands than other coloring ions like Fe. Thus, by using either Pr, Tb or a mixture thereof, a higher yield of fluorescence light can be achieved, if fluorescence of the material is desired. Elements or ions which result in a non-tooth-like fluorescence should not be contained. Thus, the following elements or ions of those elements which are typically not present include: Sm, Eu, Dy and mixtures thereof.

Beside the suitable cations mentioned above, the coloring solution described in the present text may contain in addition coloring ions selected from the Periodic Table of Elements (in the 18 columns form) that are classified as rare earth elements (including Ce, Nd, Gd, Ho, Tm, Yb and Lu) and/or from transition metals of the groups 3, 4, 5, 6, 7, 9, 10, 11.

Anions which can be used include $Cl^-$, $OAc^-$, $NO_3^-$, $NO_2^-$, $CO_3^{2-}$, $HCO_3^-$, $ONC^-$, $SCN^-$, $SO_4^{2-}$, $SO_3^{2-}$, gluturate, lactate, citrate, gluconate, propionate, butyrate, glucuronate, benzoate, phenolate, further halogen anions (e.g. bromide) and mixtures thereof.

The coloring solutions may further comprise a fluorescing component.

Fluorescing components which can be used include salts of Bi and mixtures thereof, in particular acetate, chloride, nitrate, or citrate.

The coloring solutions may further comprise a thickening agent.

Using or adding a thickening agent to the coloring solution(s) may facilitate the stabilization of the distribution of the coloring ions into the pores of the porous dental zirconia block during the treating and/or drying/immobilization steps.

The thickening agent may also help to prevent the coloring ions from being drawn to the surface of the block during the drying/immobilization process.

The thickening agent is different from the solvent.

Suitable thickening agent(s) can be characterized by at least one of the following features:
being soluble in the solvent;
average molecular weight (Mw): 200 to 100,000 g/mol or 400 to 100,000 g/mol or 1,000 to 100,000 g/mol;
being a liquid or a solid.

Using a thickening agent with the following properties can sometimes be preferred:
being soluble in the solvent;
average molecular weight (Mw): 1,000 to 50,000 g/mol.

The thickening agent typically only comprises elements selected from H, C, O, N and Hal (F, Cl, Br) and combinations thereof. The thickening agent does typically not contain S and/or P.

The thickening agent is typically free of polymerizable groups like e.g. (meth)acrylate groups or epoxy groups.

The thickening agent does typically not comprise elements which cannot be burnt out during the sintering process.

Thickening agent(s) which can be used include polyol(s) (including polyvinyl alcohol), glycol ether(s) (e.g. PEG 200, PEG 400, PEG 6000, PEG 35000, diethylene glycol methyl ether, diethylene glycol ethyl ether), di- and polyalcohol(s) (including 1,2-propanediol, 1,3-propanediol, glycerol), glycerol ether, polysaccharide(s), xanthan gum, methyl cellulose and mixtures thereof.

Polyethylene glycols which can be used can be represented by the following formula:

with $R^1$=H, Acyl, Alkyl, Aryl, Alkylaryl, Polypropylglycol, Poly-THF, preferably H, Acetyl, Methyl, Ethyl, Propyl, Butyl, Hexyl, Octyl, Nonyl, Decyl, Lauryl, Tridecyl, Myristyl, Palmityl, Stearyl, Oleyl, Allyl, Phenyl, p-Alkylphenyl, Polypropyleneglycol, Poly-THF and m=4 to 2,500, preferably 10 to 2,500, more preferably 20 to 1,250.

The coloring solution may in addition comprise an acidic component.

Adding an acidic component may help to dissolve the coloring components in the solvent.

Acidic components which can be used include HCl, $HNO_3$, acetic acid, citric acid, $H_2SO_4$ and mixtures thereof.

The coloring solutions described in the present text may also comprise one or more complexing agents.

Adding a complexing agent can be beneficial to improve the storage stability of the solution, accelerate the dissolving process of salts added to the solution and/or increase the amount of salts which can be dissolved in the solution.

The complexing agent is typically able to form a complex with the metal ions being present in the solution. The complex formed should be soluble in the solvent.

E.g., the complexing agent can be used in an at least stoichiometric ratio with respect to the molar amount of the coloring ions contained in the solution. Good results can be achieved, if the molar ratio of the complexing agent to the coloring ions is equal to or greater than about 1 or about 1.2 or about 2 or about 3.

If the amount of complexing agent used is too low, the coloring ions might not be dissolved entirely. If the amount of complexing agent used is too high, the excess complexing agent itself might remain unsolved.

The complexing agent is usually added as a separate component of the solution. However, it can also be added or be present in form of an anion of the coloring component(s).

Examples include acetylacetonate, crown ethers, cryptands, ethylene diamine triacetic acid and its salts, ethylene diamine tetraacetic acid and its salts, nitrilotriacetic acid and its salts, citric acid and its salts, triethylene tetramine, porphin, poly acrylate, poly asparagate, acidic peptides, phthalocyanine, salicylate, glycinate, lactate, propylene diamine, ascorbate, oxalic acid and its salts and mixtures thereof.

Complexing agents having anionic groups as complexing ligands can be preferred. At least parts of the complexing ligands should be anionic. Complexing agents having only uncharged complexing ligands (or even cationic ligands) like pure amines (e.g. ethylene diamine at pH values at 8 to 14) might not yield sufficiently stable solutions.

Typically, the complexing agent is present in the coloring solution in an amount sufficient to dissolve at least the coloring ions in the solvent or to prevent precipitation of these ions.

In case a complexing component is used, no acidic component is used in the same coloring solution, as this would significantly decrease the ability of the complexing component to dissolve the coloring ion(s).

The coloring solution may contain the respective components in the following amounts:

The solvent(s) may be present in the following amounts:
  Lower limit: at least 20 wt. % or at least 25 wt. % or at least 30 wt. %;
  Upper limit: utmost 99 wt. % or utmost 95 wt. % or utmost 90 wt. %;
  Range: 20 wt. % to 99 wt. % or 30 wt. % to 95 wt. %.
The coloring ion(s) may be present in the following amounts:
  Lower limit: at least 0.05 wt. % or at least 0.2 wt. % or at least 0.3 wt. %;
  Upper limit: utmost 10 wt. % or utmost 8 wt. % or utmost 5 wt. %;
  Range: 0.05 wt. % to 10 wt. % or 0.3 wt. % to 5 wt. %.
The complexing agent(s) may be present in the following amounts:
  Lower limit: at least 0.2 wt. % or at least 1 wt. % or at least 2 wt. %;
  Upper limit: utmost 35 wt. % or utmost 25 wt. % or utmost 15 wt. %;
  Range: 0.2 wt. % to 35 wt. % or 2 wt. % to 15 wt. %.
The thickening agent(s) may be present in the following amounts:
  Lower limit: at least 1 wt. % or at least 2 wt. % or at least 3 wt. %;
  Upper limit: utmost 25 wt. % or utmost 20 wt. % or utmost 15 wt. %;
  Range: 1 wt. % to 25 wt. % or 3 wt. % to 15 wt. %.
The acidic component(s) may be present in the following amounts:
  Lower limit: at least 0.001 wt. % or at least 0.01 wt. % or at least 0.1 wt. %;
  Upper limit: utmost 5 wt. % or utmost 3 wt. % or utmost 1 wt. %;
  Range: 0.001 wt. % to 5 wt. % or 0.1 wt. % to 2 wt. %.
The fluorescing component(s) may be present in the following amounts:
  Lower limit: at least 0 wt. % or at least 0.001 wt. % or at least 0.01 wt. %;
  Upper limit: utmost 1 wt. % or utmost 0.75 wt. % or utmost 0.5 wt. %;
  Range: 0 wt. % to 1 wt. % or 0.01 wt. % to 0.5 wt. %.
Unless defined otherwise, wt. % is based on the amount of the whole coloring solution.

Coloring solutions which can be used in the process described in the present text can be described as follows:

Embodiment CS1

Coloring ions: 5 to 10 wt. %,
Solvent: 55 to 72 wt. %,
Fluorescing component: 0.05 to 0.5 wt. %,
Thickening agent: 10 to 15 wt. %,
Complexing agent: 10 to 15 wt. %,
Acidic component: 0 wt. %,
wt. % with respect to the amount of the coloring solution.

Embodiment CS2

Coloring ions: 1 to 5 wt. %,
Solvent: 70 to 92 wt. %,
Fluorescing component: 0.01 to 0.3 wt. %,
Thickening agent: 3 to 15 wt. %,
Complexing agent: 2 to 8 wt. %,
Acidic component: 0 wt. %,
wt. % with respect to the amount of the coloring solution.

Embodiment CS3

Coloring ions: 5 to 10 wt. %,
Solvent: 70 to 82 wt. %,

Fluorescing component: 0.05 to 0.5 wt. %,
Thickening agent: 10 to 15 wt. %,
Complexing agent: 0 wt. %,
Acidic component: 0.05 to 2 wt. %,
wt. % with respect to the amount of the coloring solution.

Embodiment CS4

Coloring ions: 1 to 5 wt. %,
Solvent: 75 to 95 wt. %,
Fluorescing component: 0.01 to 0.3 wt. %,
Thickening agent: 3 to 15 wt. %,
Complexing agent: 0 wt. %,
Acidic component: 0.5 to 3 wt. %,
wt. % with respect to the amount of the coloring solution.

If two different coloring solutions are used, these coloring solutions typically differ with respect to their concentration of coloring components. However, when infiltrating a porous block, using acidic solutions or complex-based solutions is typically recommended. Combination of different stabilization mechanisms may lead to undesired precipitation of the coloring ions.

The coloring solution can be produced by mixing its components. This can be done at room temperature or by applying heat and/or while stirring.

Applying heat and/or stirring can be beneficial in order to accelerate the dissolution process of the coloring ions into the solvent.

The composition is typically stirred until all solid components are completely dissolved in the solvent.

Undesired precipitations can be removed by filtering.

The porous dental zirconia block described in the present text, which is obtained or obtainable after an immobilization step has been applied can typically be characterized by the following features alone or in combination:
a) BET surface: 5 to 15 $m^2/g$ or 5.5 to 11 $m^2/g$;
b) density: 2.5 to 4 $g/cm^3$ or 2.85 to 3.35 $g/cm^3$;
c) biaxial flexural strength: 15 to 55 MPa determined according to ISO 6872:2015 adapted to measurement in porous state (measurement set up: 3.6 mm punch diameter, 0.1 mm/min load speed, 17 mm sample diameter, 2 mm sample thickness, support ball diameter 6 mm);
d) Vickers hardness: 15 to 150 (HV 0.5) or 20 to 140 (HV 0.5);
e) coefficient of thermal expansion: $8.5*10^{-6}$ $K^{-1}$ to $11.5*10^{-6}$ $K^{-1}$.

The following combination of features is sometimes preferred: a) and b); a) and c); a), b) and c).

Compared to the properties of the porous dental zirconia block before the treating and immobilization steps, the properties of the porous dental zirconia block after applying the treating and immobilization steps do not significantly change.

The porous dental zirconia block can be fixed to a holding device, which allows the fixation of the block in a milling machine.

Fixing of the dental zirconia block to a holding device can be affected by clamping, gluing, screwing and combinations thereof.

Useful holding devices include frames (open and closed), stubs or mandrels. Using a holding device may facilitate the production of dental articles and restorations with a machining device.

Examples of useful holding devices are described in U.S. Pat. No. 8,141,217 B2 (Gubler et al.), WO 02/45614 A1 (ETH Zurich), DE 203 16 004 U1 (Stuehrenberg), U.S. Pat. No. 7,985,119 B2 (Basler et al.) or WO 01/13862 (3M). The content of these documents with respect to the description of the holding device is herewith incorporated by reference.

The invention also relates to a process of producing a dental zirconia restoration.

This process comprises the steps of
providing the porous dental zirconia block described in the present text;
machining a porous dental restoration from this block; and
sintering the porous dental restoration, preferably to or close to the theoretically achievable density.

Thus, the porous dental zirconia block obtained or obtainable by the process described in the present text is particularly useful for machining a dental restoration out of that block.

The machining can be done either in a dental lab or chair-side, that is in the office of the dentist.

The machining step can be done with a milling, drilling, cutting, carving, or grinding device. Those devices are commercially available e.g. from Roland (DMX™ mills), or Sirona (CEREC™ inLab CAD/CAM) and others.

Useful milling parameters include: rotary speed of milling tool: 5,000 to 40,000 revolutions/min; feed rate: 20 to 5,000 mm/min; milling cutter diameter: 0.8 to 4 mm.

If desired, the machined porous dental zirconia restoration is cleaned, e.g. by removing milling dust with pressurized air.

The porous dental article or restoration is sintered by applying a heat treatment step.

The heat treatment is typically conducted in a temperature range and for a sufficient time to obtain a fully sintered article.

Generally, the sintering or firing conditions are adjusted such that the sintered dental ceramic article has a density of equal or greater than about 98% compared with the theoretically achievable density.

During the firing process the porous dental article is sintered to its final shape, thereby undergoing changes with regard to dimension, density, hardness, bending strength and/or grain size.

The dwell time (that is the time during which the article is kept at a particular temperature) is not really critical. The dwell time can be zero. The dwell time, however, can also be in a range of 0.1 to 24 h or 0.02 to 5 h.

The firing temperature and dwell time are typically correlated. A higher temperature typically requires only a short dwell time. Thus, the dwell time, may last from 0.02 to 5 h (e.g. if the firing temperature is 1,550° C.) or from 0.1 to 24 h (e.g. if the firing temperature is 1,100° C.).

Useful sintering conditions can be characterized by one or more of the following parameters:
temperature: 900° C. to 1,600° C. or 1,000° C. to 1,500° C. or 1,100° C. to 1,450° C. or 1,000° C. to 1,300° C. or 1,300° C. to 1,600° C. or 1,400° C. to 1,580° C. or 1,450° C. to 1,580° C.;
atmosphere: air or inert gas (e.g. nitrogen, argon);
duration: until a density of at least 98 or 99 of the theoretically achievable density of the material has been reached;
dwell time: 0.1 to 24 h or 0 to 5 h;
pressure: ambient pressure.

A respective sintering protocol can be characterized as follows:
sintering temperature: 1,350 to 1,600° C.;
duration: 50 to 480 min;
heating rate: 1 to 30° C./min.

If a fast sintering is desired (which is sometimes preferred), the following sintering conditions can be applied:

The overall time needed for heat treating and cool-down the dental zirconia article is typically 60 min or less, 40 min or less, 30 min or less.

The overall time typically also depends to some extent on the volume of the zirconia article to be sintered.

Large articles typically require a longer heat treating time than smaller articles.

An oven which can be used for the process described in the present text is commercially available from Dentsply Sirona (SpeedFire™) A suitable furnace is also described in WO 2017/144644 A1 (Sirona). This furnace is for carrying out a heat treatment of a dental replacement part and comprises an induction coil, a radiant heater, an insulation layer and a furnace chamber. Further, the furnace has a cooling system to control the internal temperature of the furnace chamber.

Generally, useful heat treating conditions which are applied during a fast-sintering process can be characterized by the following features alone or in combination:
a) heating rate: 1 to 7 K/sec or 3 to 7 K/sec;
b) sintering temperature: at least 1,350° C. or at least 1,450° C. or at least 1,500° C.;
c) atmosphere: air or inert gas (e.g. nitrogen, argon);
d) duration: until a density of at least 98 or at least 99% of the theoretically achievable density of the material has been reached;
e) dwell time: 0 to 8 min or 0 to 5 min;
f) pressure: ambient pressure.

A combination of the following features is sometimes preferred: a) and b); a), b) and d); a), b), c), d) and e).

Even, if the theoretical density of a sintered zirconia material depends to a certain degree on the amount of further oxides present (e.g. yttria and/or alumina), for the present text the theoretically achievable density of the sintered zirconia material is defined as 6.08 g/cm$^3$ independent of the presence of further oxides.

Further useful embodiments are described below:

Embodiment 1

A process for treating a porous dental zirconia block with a coloring solution as described in any of the preceding claims, the process comprising the steps of
providing a porous dental zirconia block having two opposing surfaces, surface U and surface L,
treating the upper surface U of the porous dental zirconia block with a coloring solution $A_1$, wherein
the coloring solution is provided with a volume $V_{A1}$,
turning the porous dental zirconia block around,
treating the now upper surface L of the porous dental zirconia block with a coloring solution $A_2$,
wherein the coloring solution is provided with a volume $V_{A2}$,
wherein the coloring solutions $A_1$ and $A_2$ comprise a solvent and coloring ions,
wherein coloring solution $A_1$ and coloring solution $A_2$ are different,
wherein the volume of at least one of the coloring solutions $A_1$ or $A_2$ is applied in portions,
wherein the following condition is met: $V_0=\Sigma V_{Ax}$ with x≥2, in particular $V_0=V_{A1}+V_{A2}$, with $V_0$ being the overall amount of coloring solution used to infiltrate the porous dental zirconia block, the porous dental zirconia block being characterized by a $ZrO_2$ content of 91 to 98 mol %, $HfO_2$ content of 0 to 2 mol %, $Y_2O_3$ content of 2 to 6 mol %, $Al_2O_3$ content of 0 to 1 mol % and a BET surface of 5 to 20 m$^2$/g.
the coloring solutions $A_1$ and $A_2$ comprising at least two of Er, Fe, Tb, Pr, Co, Mn and Cr ions and having viscosity in the range of 1 to 20 mPa*s at 23° C.

Embodiment 2

A process for treating a porous dental zirconia block with a coloring solution as described in any of the preceding claims, the process comprising the steps of
providing a porous dental zirconia block having two opposing surfaces, surface U and surface L,
treating the upper surface U of the porous dental zirconia block with a coloring solution A1, wherein
the coloring solution is provided with a volume VA1,
turning the porous dental zirconia block around,
treating the now upper surface L of the porous dental zirconia block with a coloring solution $A_2$,
wherein the coloring solution is provided with a volume $V_{A2}$,
wherein the coloring solutions A1 and A2 comprise a solvent and coloring ions,
wherein coloring solution A1 and coloring solution A2 are different,
wherein the volume of at least one of the coloring solutions A1 or A2 is applied in portions,
wherein the following condition is met: $V_0=\Sigma V_{Ax}$ with x≥2, in particular $V_0=V_{A1}+V_{A2}$, with $V_0$ being the overall amount of coloring solution used to infiltrate the porous dental zirconia block,
the porous dental zirconia block being characterized by a $ZrO_2$ content of 91 to 98 mol %, $HfO_2$ content of 0 to 2 mol %, $Y_2O_3$ content of 2 to 6 mol %, $Al_2O_3$ content of 0 to 1 mol % and a pore volume of 0.12 to 0.18 ml/g.
the coloring solutions $A_1$ and $A_2$ comprising at least two of Er, Fe, Tb, Pr, Co, Mn and Cr ions and having viscosity in the range of 1 to 20 mPa*s at 23° C.

Embodiment 3

A process for treating a porous dental zirconia block with a coloring solution as described in any of the preceding claims, the process comprising the steps of
providing a porous dental zirconia block having two opposing surfaces, surface U and surface L,
treating the upper surface U of the porous dental zirconia block with a coloring solution A1, wherein
the coloring solution is provided with a volume VA1,
turning the porous dental zirconia block around,
treating the now upper surface L of the porous dental zirconia block with a coloring solution A2,
wherein the coloring solution is provided with a volume VA2,
wherein the coloring solutions A1 and A2 comprise a solvent and coloring ions,
wherein coloring solution A1 and coloring solution A2 are the same,
wherein the volume of at least one of the coloring solutions $A_1$ or $A_2$ is applied in portions,
wherein the following condition is met: $V_0=\Sigma V_{Ax}$ with x≥2, in particular $V_0=V_{A1}+V_{A2}$, with $V_0$ being the overall amount of coloring solution used to infiltrate the porous dental zirconia block,
the porous dental zirconia block being characterized by a $ZrO_2$ content of 91 to 98 mol %, $HfO_2$ content of 0 to 2 mol %, $Y_2O_3$ content of 2 to 6 mol %, $Al_2O_3$ content of 0 to 1 mol % and a pore volume of 0.12 to 0.18 ml/g.

the coloring solutions $A_1$ and $A_2$ comprising at least two of Er, Fe, Tb, Pr, Co, Mn and Cr ions and having viscosity in the range of 1 to 20 mPa*s at 23° C.

The dental zirconia restoration obtainable or obtained by the process described in the present text can typically be characterized by the following features alone or in combination:

- a) density: at least 98 or at least 99% of theoretical density
- b) biaxial flexural strength: 500 to 1,500 MPa or 800 to 1,400 MPa, determined according to ISO 6872:2015;
- c) phase content tetragonal phase: 30 to 90 wt. % or 40 to 80 wt. % or 45 to 80 wt. %;
- d) translucency: 25% or more, determined on a sample having a thickness of 1 mm in reflection mode averaged over a wavelength range of 400 to 700 nm;
- e) being tooth colored.

A combination of the following features is sometimes preferred: a) and b); a) and c); a) and d); a), b) and c); or a), b), d) and e).

According to one embodiment, the sintered dental zirconia article is characterized by the following features in combination:

- a) density: at least 99 percent of theoretical density;
- b) biaxial flexural strength: 800 to 1,400 MPa, determined according to ISO 6872:2015;
- c) translucency: 25% or more, determined on a sample having a thickness of 1 mm in reflection mode averaged over a wavelength range of 400 to 700 nm.

The respective measurements are typically done on test samples as described in the respective standards. The coloring solution described in the present text do typically not contain components in an amount which is toxic or otherwise detrimental to a patient's health.

According to one embodiment, the coloring solution does not comprise at least one or all of the following components:

ions selected from Dy, Sm, Eu, Cu, Mo or combinations thereof, each in an amount above about 0.01 wt. % or above about 0.005 wt. % or above about 0.001 wt. %, wt. % with respect to the weight of the coloring solution;

solid particles settling from the solution upon storage for more than about 2 h.

Thus, the solution described in the present text is essentially free of the ions mentioned above or only may contain unavoidable traces of these ions which may be present in the raw materials used.

Further, the solution does typically also not comprise solid particles which may or will remain on the surface of a porous zirconia block once the coloring solution is applied to the surface of the porous zirconia block. Thus, the solution described in the present text is neither a dispersion of solid particles in a solvent nor a slurry.

The process of the present invention does also typically not require the need for the covering of the surface of the block with a casing material, and/or for the application of pressure (negative or positive) during the infiltrating of the coloring solution into the porous zirconia material.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope thereof.

The following examples are given to illustrate the invention.

EXAMPLES

Unless otherwise indicated, all parts and percentages are on a weight basis, all water is de-ionized water (DI water), and all molecular weights are weight average molecular weight. Moreover, unless otherwise indicated all experiments were conducted at ambient conditions (23° C.; 1013 mbar).

Methods

Viscosity

If desired, the viscosity of liquids can be measured using a Physica MCR 301 Rheometer (Anton Paar, Graz, Austria) with a cone/plate geometry CP25-1 under controlled shear rate at 23° C. (e.g. 616 $s^{-1}$). The diameter is 25 mm, the cone angle 1°, and the separation between the cone tip and the plate 49 µm.

pH Value

If desired, the pH value of water-based solutions can be determined with generic pH test strips, according to the test strips' instruction for use.

Elemental Composition

If desired, the elemental composition can be determined by X-ray fluorescence spectrometry (XRF), e.g. with the ZSX Primus II from Rigaku, Japan. This method is especially suited for the analysis of solids, e.g. zirconia ceramics or glass materials.

Fluorescence

If desired, the samples are placed in an UV-light box used for inspection of e.g. thin layer chromatography plates. Fluorescence can be detected by the human eye by the lightening up of the sample against the black background.

BET Surface

If desired, the BET surface of a porous article can be determined as follows: Total pore volume and average pore diameter can be analyzed with the use of $N_2$ sorption isotherms and BET surface area analysis. Samples of around 0.1-2 grams can be cut (if necessary) from larger samples in order to be inserted in to the sample tubes. All samples are degassed in vacuum for more than 1 h at 120° C. before analysis. The samples are then analyzed by adsorption and desorption of $N_2$ gas with a Belsorb II (distributed by Robotherm Präzisionsmesstechnik, Bochum, Germany) in a 9 mm cell with 2 cm bulb and with a 5 mm glass rod. At temperature of liquid nitrogen, absorption data points are collected from 0.1 to 0.99 p/p0 and desorption points collected from 0.99 to 0.5 p/p0. The specific surface area S is calculated by the BET method at p/p0 0.25-0.3 (details regarding calculation see Belsorb Analysis Software User Manual Operating Manual, Chapter 12, Bel Japan. INC).

Density

If desired, the density of the material can be measured by an Archimedes technique. The measurement is made on a precision balance (identified as "BP221S" from Sartorius AG, Göttingen, Germany) using a density determination kit (identified as "YDK01" from Sartorius AG). In this procedure, the sample is first weighed in air (A), then immersed in a solution (B). The solution is a 0.05 wt. % tenside solution (e.g. "Berol 266", Fa. Hoesch) in DI water. The density is calculated using the formula $\rho=(A/(A-B))\ \rho 0$, where $\rho 0$ is the density of water.

In the case that the material possesses a regular shape (e.g. of a cuboid), the density can simply be determined by measuring the dimensions x, y, and z (e.g. with a sliding caliper (identified as "IP67" from Mitutoyo, Japan)) and the weight m of the sample (e.g. with a precision balance (identified as "BP221S" from Sartorius AG, Göttingen, Germany)). The density is calculated using the formula $\rho=m/(x*y*z)$.

Porosity

If desired, the porosity can be determined as follows: Porosity=(1−(density of porous material/density of sintered material))×100. As described above ("Density" section), the density of the porous material can be calculated by the division of weight and volume. Volume can be obtained by geometrical measurements.

Pore Volume:

The pore volume of a porous zirconia body $V_P$ can be determined by subtracting the volume of the zirconia material in the porous body ($V_Z$=weight of the porous body/density of the zirconia material) from the entire volume of the porous body (e.g. $V_B=x*y*z$): $V_P=V_B-V_Z$. For the present text, the density of the sintered zirconia material is defined as 6.08 g/cm$^3$. This value is considered sufficiently precise for determining the pore volume of a porous zirconia body.

Average Grain Size

If desired, the average grain size can be determined with the Line Intercept Analysis. FESEM micrographs with 70,000 times magnification are used for grain size measurement. Three or four micrographs taken from different areas of the sintered body are used for each sample. Ten horizontal lines, which are spaced at roughly equal intervals across the height of each micrograph, are drawn. The numbers of grain boundary intercepts observed on each line are counted and used to calculate the average distance between intercepts. The average distance for each line is multiplied by 1.56 to determine the grain size and this value is averaged over all the lines for all micrographs of each sample.

Biaxial Flexural Strength

If desired, the biaxial flexural strength of pre-sintered material can be determined according to ISO 6872:2015 with the following modifications: The pre-sintered sample is sawn into wafers with a thickness of 2+/−0.1 mm using a dry cut saw. The diameter of the samples should be 17+/−2 mm. The parallel large faces of the wafer are ground using silicon carbide sand paper (P2500). Each wafer is centred on a support of three steel balls (diameter of the balls 6 mm) with a support diameter of 14 mm. The punch diameter in contact with the wafer is 3.6 mm. The punch is pushed onto the wafer at a rate of 0.1 mm per min. A minimum of 15 samples is measured to determine the average strength. The tests can be conducted using an Instron 5566 universal testing machine (Instron Deutschland GmbH).

Vickers Hardness

If desired, the Vickers hardness can be determined according to ISO 14705 with the following modifications: The surface of the pre-sintered samples is ground using silicon carbide sand paper (P2500). The surface of the sintered samples is polished with 20 μm diamond suspension. The test forces are adjusted to the hardness level of samples. Used test forces can be between 0.2 kg and 2 kg and are applied for 15 s each indentation. A minimum of 10 indentations is measured to determine the average Vickers hardness. The tests can be conducted with a hardness tester Leco M-400-G (Leco Instrumente GmbH).

Method for Measuring Translucency

If desired, the translucency of the ceramic articles can be evaluated with the following procedure: A test piece in the shape of a disc with an approximate thickness of 1±0.05 mm and an area of measurement of at least 10 mm in diameter is provided. For preparation of the test pieces the pre-sintered sample is sawn into wafers with a thickness of approximately 1.3 mm using a dry cut saw. The parallel large faces of the wafer are ground using silicon carbide sand paper (P2500). The ground samples are sintered in an appropriate furnace to a sintered sample with a thickness of 1±0.05 mm. The sintered sample is measured as fired with a spectrophotometer (X-Rite Color i7, Grand Rapids, USA) in reflectance mode against a white and a black background to obtain the opacity (contrast ratio) of the material. The translucency T is calculated according to T=100%−opacity (in percent). Higher values of translucency are indicative of greater transmission of light, and less opacity.

L*a*b* Values

If desired, L*a*b* values can be determined using the same equipment and method which is used for determining the opacity (contrast ratio) and translucency.

Materials

TABLE 1

| | |
|---|---|
| 4Y-TZP powder; alumina content 0.08 wt. %; powder density 1.6 g/cm$^3$; BET (without binder) 8 m$^2$/g; binder amount 3 wt. % (4 mol % yttria) | Un-colored zirconia powder |
| Erbium(III)chloride Hydrate | Coloring component |
| Terbium(III)chloride Hydrate | Coloring component |
| Chromium(III)chloride Hexahydrate | Coloring component |
| Bismuth(III)oxychloride | Fluorescing component |
| Erbium(III)citrate solution | Coloring component |
| Terbium(III)citrate solution | Coloring component |
| Manganese(II)acetate Tetrahydrate | Coloring component |
| PEG 35000; Polyethylene glycol; Mw: 35,000 g/mol | Thickening agent |
| PEG 6000; Polyethylene glycol; Mw: 6,000 g/mol | Thickening agent |
| Hydrochloric acid | Acidic component |

General Procedure for Producing Coloring Solutions

The components are weighed and then all put together in a container. The components are mixed with a magnetic stirrer, until all solid components are dissolved and the solution is clear.

General Procedure for Producing Porous Dental Zirconia Blocks Blocks are prepared by providing un-colored zirconia powder (4Y-TZP) and pressing it uniaxially within a pressure range of 30 to 50 kN to dimensions of 20.6 mm×19.6 mm×16.0 mm. The pressed blocks are then de-bindered and pre-sintered in one step. This is done using the following conditions: 1K/min to 900° C.; 1 hour hold. The unshaded, dry and porous zirconia block is placed on a table, so that the two surfaces with dimensions 20.6 mm×19.6 mm (as pressed) represent the upper (U) and the lower (L) surfaces. The block has a density of 3.2 g/cm3 and a pore volume per mass of 0.147 ml/g.

General Procedure for Treating Porous Dental Zirconia Blocks A porous, pre-sintered zirconia mill blank is provided. The first solution is applied onto the blank until the entire upper surface of the blank is covered with the liquid. The surface tension makes it rather simple to avoid that the liquid flows down at the sides of the blank. It is easy to "pile up" the liquid to about 0.5 to 1 mm height on the blank. As the solution is drawn into the pores of the blank, more liquid is applied until the planned first volume to be applied is reached. Then the blank is turned upside down and the process repeated with the second liquid until the planned second volume to be applied is reached. The blank is left in that position for a certain amount of time to let it dry. Then the remaining water, thickening agent and anions are removed by application of a heat treatment step.

General Procedure for Sintering Porous Dental Zirconia Blocks

After the heat treatment step, the shading process of the blanks is finished. After that, dental restorations can be milled out of the blocks and fired to full density (e.g. 10K/min to 1,500° C.; 2 hours hold).

In the examples, the shaded blanks are cut horizontally into slices of about 1.3 mm thickness. The slices are sintered to full density (10K/min to 1,500° C.; 2 hours hold) and analyzed for color.

Preparation of a Complex-Based Shading Liquid

A shading liquid containing erbium(III) citrate, terbium (III) citrate, manganese(II) acetate tetrahydrate, PEG 35000 and DI water is prepared.

For this, 12.00 g erbium(III) citrate solution (6.6 wt. % erbium), 4.00 g terbium(III) citrate solution (4.0 wt. % terbium), 0.02 g manganese(II) acetate tetrahydrate salt, 1.60 g PEG 35000 and 22.38 g DI water are mixed until a clear solution is obtained ("CSL"). The liquid has a viscosity of 4.73 mPa*s and a pH value of 8.

Preparation of Acidic Shading Liquids

Three shading liquids containing erbium(III) chloride, terbium(III) chloride, chromium(III) chloride, bismuth(III) oxychloride, PEG 35000, PEG 6000, hydrochloric acid and DI water are prepared.

For this, 5.00 g erbium(III) chloride hydrate salt, 0.28 g terbium(III) chloride hydrate salt, 0.02 g chromium(III) chloride hexahydrate salt, 0.12 g bismuth(III) oxychloride salt, 0.80 g PEG 35000, 4.00 g PEG 6000, 2.00 g hydrochloric acid (25%) and 27.78 g DI water are mixed until a clear solution is obtained. This is the "body" shade liquid ("ASL-B"). The liquid has a viscosity of 8.38 mPa*s and a pH value of 0.

Also, 1.40 g erbium(III) chloride hydrate salt, 0.08 g terbium(III) chloride hydrate salt, 0.01 g chromium(III) chloride hexahydrate salt, 0.09 g bismuth(III) oxychloride salt, 0.80 g PEG 35000, 4.00 g PEG 6000, 2.00 g hydrochloric acid (25%) and 31.62 g DI water are mixed until a clear solution is obtained. This is the "enamel" shade liquid ("ASL-E"). The liquid has a viscosity of 8.23 mPa*s and a pH value of 0.

Further, 0.12 g bismuth(III) oxychloride salt, 0.80 g PEG 35000, 4.00 g PEG 6000, 4.00 g hydrochloric acid (25%) and 33.08 g DI water are mixed until a clear solution is obtained. This is the "white" shade liquid ("ASL-W"). The liquid has a viscosity of 7.35 mPa*s and a pH value of 0.

Inventive Example (IE) 1: Complex-Based Shading Liquid, Monochrome 1.6 ml of liquid CSL are dropped onto the upper surface of the block in portions of 8 drops with a pipette. A new portion is applied when the previously applied liquid has almost completely infiltrated the block. The block is then turned upside-down and another 1.6 ml liquid CSL are applied in the same manner as before.

Inventive Example 2: Acidic Shading Liquid, Monochrome 1.6 ml of liquid ASL-B are dropped onto the upper surface of the block in portions of 8 drops with a pipette. A new portion is applied when the previously applied liquid has almost completely infiltrated the block. The block is then turned upside-down and another 1.6 ml liquid ASL-B are applied in the same manner as before.

Inventive Example 3: Acidic Shading Liquid, Shade Gradient 1.6 ml of liquid ASL-B are dropped onto the upper surface of the block in portions of 8 drops with a pipette. A new portion is applied when the previously applied liquid has almost completely infiltrated the block. The block is then turned upside-down and 1.6 ml liquid ASL-E are applied in the same manner as before.

Inventive Example 4: Acidic Shading Liquid, Shade Gradient 1.6 ml of liquid ASL-B are dropped onto the upper surface of the block in portions of 8 drops with a pipette. A new portion is applied when the previously applied liquid has almost completely infiltrated the block. The block is then turned upside-down and 1.6 ml liquid ASL-W are applied in the same manner as before.

Inventive Example 5: Acidic Shading Liquid, Shade Gradient 1.5 ml of liquid ASL-E are dropped onto the upper surface of the block in portions of 8 drops with a pipette. A new portion is applied when the previously applied liquid has almost completely infiltrated the block. After that, 1.5 ml of liquid ASL-B are applied onto the upper surface of the block in the same manner as before. The block is then turned upside-down and 0.2 ml liquid ASL-W are applied.

Further Treatment

The remaining water, PEG and anions are removed by application of a heat treatment step: 5K/min to 950° C., 1 hour hold.

A first set of blocks 1-1 to 1-5 is heat treated immediately after the infiltration of the last block was finished.

A second set of blocks 2-1 to 2-5 is heat treated 24 hours after the infiltration of the last block was finished.

The blanks are then cut into platelets of about 1.3 mm thickness (parallel to the two infiltration surfaces), and the platelets are sintered to full density (10K/min to 1500° C., 2 hours hold) to check the shading result throughout the block by measurement with a Color i7 from X-rite.

Table 2 shows the time that it took for the liquids to infiltrate the blocks, as well as the time between the end of the infiltration and the start of the heat treatment. Since more than one block per experiment was infiltrated, time-ranges are given in which the fastest and slowest block are included. The five blocks of the first set and the five blocks of the second set were heat treated in the same furnace run respectively. Therefore, the faster infiltrated blocks have a longer waiting time than the slower infiltrated blocks.

Figure 2:
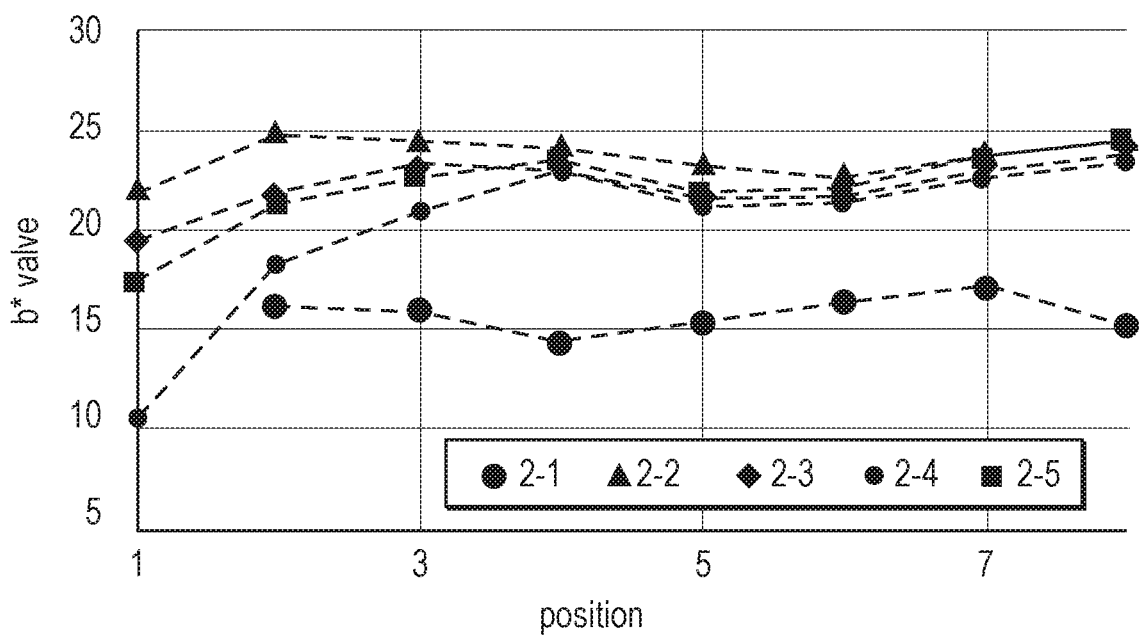

In FIGS. 1 and 2 the results are illustrated by plotting the determined b* value against the position in the block (i.e. number of the platelet). Samples 1-3, position 3 and 2-1, position 1 were lost in the cutting process and could not be measured.

FIG. 1 shows the first set with low waiting time; FIG. 2 shows the second set with additional 24 hours waiting time between infiltration and heat treatment.

TABLE 2

|       | approximate infiltration time of 1st side/min | approximate infiltration time of 2nd side/min | approximate waiting time until heat treatment/h |
|-------|----|----|----|
| IE 1-1 | 16-18   | 20-25 | 2  |
| IE 1-2 | 50-55   | 50-60 | 1  |
| IE 1-3 | 50-55   | 40-50 | 1  |
| IE 1-4 | 50-55   | 30-40 | 1  |
| IE 1-5 | 120-135 | 4-5   | 0  |
| IE 2-1 | 16-18   | 20-25 | 26 |
| IE 2-2 | 50-55   | 50-60 | 25 |
| IE 2-3 | 50-55   | 40-50 | 25 |
| IE 2-4 | 50-55   | 30-40 | 25 |
| IE 2-5 | 120-135 | 4-5   | 24 |

The b* value (yellow color) obtained from the performed measurements was used for evaluating the shading result, since this parameter is considered suited to determine the intensity of the resulting shade.

For a monochrome block, a constant b* value over the platelets would be expected. For the graded blocks, a decrease of the b* value at low platelet numbers would be expected, as this is where the liquids with lower ion concentration (ASL-E and ASL-W) were applied.

FIG. 1 shows that IE 1-1 and 1-2 have a quite constant b* value throughout the block, as expected. From the graded samples, only 1-4 with the most pronounced gradient (liquids ASL-B and ASL-W) has the expected obvious decrease in b* value towards lower platelet numbers.

FIG. 2 shows that the variations of the b* values have decreased and therefore the shading result has further stabilized. Now, IE 1-1 and 1-2 show an even better constancy of the b* value over the different platelets. The graded samples have a good constancy from platelets 4 to 8 and a gradient from platelets 1 to 3. IE 2-4 again has the most pronounced gradient. IE 2-5 shows that the shade of the uppermost layer (platelet 1) could even be fine-tuned to a slightly lower b* value by application of all three ASL liquids in comparison to IE 2-3, where only ASL-B and ASL-E were used.

Comparison of the first and the second set of blocks shows that a certain waiting time between infiltration and heat treatment can be beneficial to homogenize the shading effect. On the other hand, this also means that the steepness of the gradient is slightly diminished by diffusion of the ions (b* values from 6 to 24 for IE 1-4 and b* values from 11 to 24 for IE 2-4).

Regarding processing time, it can be preferable to infiltrate equal amounts of liquids from both sides of the block, because infiltration time typically increases when more liquid is applied from a single side. IE 1-2, IE 1-3 and IE 1-4 needed only approx. 80 to 115 min for complete infiltration, while IE 1-5 needed approx. 125 to 140 min.

The chemistry of the liquids sometimes also has an influence on the infiltration time. The less ions and thickener a solution contains, the faster the coloring solution typically can infiltrate into a block. However, the use of a certain amount of thickener can be beneficial to reduce the risk of drying artifacts towards the rim of the blocks.

In IE 1-1 (using a complex-based shading liquid that contained a small amount of thicker) the infiltration was completed in approx. 35 to 45 min, which is faster compared to the examples where acidic shading liquids containing more thickener were used.

The invention claimed is:

1. A process for treating a porous dental zirconia mill block with a coloring solution, the process comprising the steps of:
   providing a porous dental zirconia mill block having two opposing surfaces, surface U and surface L,
   treating the surface U of the porous dental zirconia mill block with a coloring solution $A_1$, wherein the surface U corresponds to an upper surface of the porous dental zirconia mill block when the surface U is being treated with the coloring solution $A_1$, and wherein the coloring solution $A_1$ is provided with a volume $V_{A1}$,
   turning the porous dental zirconia mill block around about an axis parallel to at least one of the two opposing surfaces to reduce a migration distance for the coloring solution $A_1$ through the porous dental zirconia mill block compared to a distance between surface U and surface L, and
   treating the surface L of the porous dental zirconia mill block with a coloring solution $A_2$, wherein upon turning the porous dental zirconia mill block the surface L corresponds to the upper surface of the porous dental zirconia mill block when the surface U is being treated with the coloring solution $A_2$, and wherein the coloring solution $A_2$ is provided with a volume $V_{A2}$,
   wherein the volume of at least one of the coloring solutions $A_1$ or $A_2$ is applied in discrete portions incrementally to ensure uniform spread and absorption,
   wherein the following condition is met: $V_0 = \Sigma V_{Ax}$ with $x \geq 2$,
   with $V_0$ being an overall amount of coloring solutions used to infiltrate the porous dental zirconia mill block.

2. The process according to claim 1, further comprising immobilizing coloring ions inside the porous dental zirconia mill block by applying a heat treatment of at least 500° C.

3. The process according to claim 1, wherein the porous dental zirconia mill block has a pore volume $V_B$, $V_B$ being larger or the same as the overall amount of coloring solution $V_0$ used for infiltrating the porous dental zirconia mill block.

4. The process according to claim 1, a coloring solution $A_3$ being applied to surface U of the porous dental zirconia mill block before the porous dental zirconia mill block is turned around, coloring solution $A_3$ being different from coloring solution $A_1$ or $A_2$,
   wherein the volume of at least one of the coloring solutions $A_1$, $A_2$ or $A_3$ is applied in portions,
   wherein the following condition is met: $V_0 = \Sigma V_{Ax}$ with $x \geq 2$,
   with $V_0$ being the overall amount of coloring solutions used to infiltrate the porous dental zirconia mill block.

5. The process according to claim 1, the porous dental zirconia mill block having a geometrically defined shape, wherein the geometrically defined shape includes a disc or cylinder.

6. The process according to claim 1, wherein the porous dental zirconia mill block, before the treating steps, comprises the respective components in the given amounts:
   a. $ZrO_2$ content: 91 to 98 mol %,
   b. $HfO_2$ content: 0 to 2 mol %,
   c. $Y_2O_3$ content: 2 to 6 mol %,
   d. $Al_2O_3$ content: 0 to 1 mol %.

7. The process according to claim 1, the porous dental zirconia mill block before treatment being characterized by the following features alone or in combination:
   BET surface: 5 to 20 $m^2/g$;
   density: 2.5 to 4 $g/cm^3$;

average connected pore diameter: 20 to 150 nm;
pore volume: 0.12 to 0.18 ml/g;
flexural strength: 15 to 55 MPa determined according to ISO 6872:2015 adapted to measurement in porous state using the following measurement set up: 3.6 mm punch diameter, 0.1 mm/min load speed, 17 mm sample diameter, 2 mm sample thickness, support ball diameter 6 mm; or
Vickers hardness: 15 to 150 (HV 0.5).

8. The process according to claim 1, at least one of the coloring solutions comprising at least two of Er, Fe, Tb, Pr, Co, Mn and Cr ions, but not comprising Ni, Mo, V ions in an amount above 0.01 wt. % with respect to the weight of the coloring solution.

9. The process according to claim 1, wherein at least one of the coloring solutions further comprises a fluorescing component in an amount of 0.01 to 1 wt. % with respect to the amount of the respective coloring solution.

10. The process according to claim 1, wherein at least one of the coloring solutions comprises a thickening agent, the thickening agent being characterized by the following features alone or in combination:
being soluble in a solvent; or
having a molecular weight (Mw) of 200 to 100,000 g/mol.

11. The process according to claim 1, the process comprising the steps of:
providing a porous dental zirconia mill block having two opposing surfaces, surface U and surface L, and
providing at least two coloring solutions, the at least two coloring solutions including coloring solution $A_1$ and coloring solution $A_2$,
wherein the coloring solutions $A_1$ and $A_2$ both comprise coloring ions and a solvent for dissolving the coloring ions, and
wherein a first concentration of the coloring ions in coloring solution $A_1$ is different from a second concentration of the coloring ions in coloring solution $A_2$.

12. The process according to claim 1, wherein the porous dental zirconia mill block is characterized by a ZrO2 content of 91 to 98 mol %, HfO2 content of 0 to 2 mol %, Y2O3 content of 2 to 6 mol %, Al2O3 content of 0 to 1 mol % and having a BET surface of 5 to 20 m2/g, and
wherein the coloring solutions $A_1$ and $A_2$ comprise at least two of Er, Fe, Tb, Pr, Co, Mn and Cr ions and having a viscosity in a range of 1 to 20 mPa*s at 23° C.

13. The process according to claim 1, the porous dental zirconia mill block to sintering by applying either of the following heat treatment steps:
sintering temperature 1,350 to 1,600° C., heating rate 1 to 7° C./sec;
sintering temperature 1,350 to 1,600° C., heating rate 1 to 30° C./min.

* * * * *